United States Patent [19]
Kingston

[11] Patent Number: 5,830,417
[45] Date of Patent: Nov. 3, 1998

[54] METHOD AND APPARATUS FOR MICROWAVE ASSISTED CHEMICAL REACTIONS

[75] Inventor: Howard M. Kingston, Evans City, Pa.

[73] Assignee: Duquesne University of the Holy Ghost, Pittsburgh, Pa.

[21] Appl. No.: 840,256

[22] Filed: Apr. 14, 1997

Related U.S. Application Data

[60] Division of Ser. No. 458,757, Jun. 2, 1995, which is a continuation-in-part of Ser. No. 357,097, Dec. 15, 1994, abandoned, which is a continuation of Ser. No. 127,263, Sep. 24, 1993, abandoned.

[51] Int. Cl.$^6$ .................................................. B01J 19/12
[52] U.S. Cl. ...................................... 422/486.29; 422/186
[58] Field of Search ............................... 422/186, 186.29

[56] References Cited

U.S. PATENT DOCUMENTS

| | | | |
|---|---|---|---|
| 4,963,709 | 10/1990 | Kimrey, Jr. | 219/10.55 |
| 4,980,039 | 12/1990 | Aysola et al. | 204/157.43 |
| 5,059,400 | 10/1991 | Benezech et al. | 422/186 |
| 5,122,633 | 6/1992 | Moshammer et al. | 219/10.55 |
| 5,204,065 | 4/1993 | Floyd | 422/113 |
| 5,215,715 | 6/1993 | Haswell et al. | 422/81 |
| 5,320,804 | 6/1994 | Zakaria et al. | 422/21 |
| 5,518,637 | 5/1996 | Myers | 210/760 |
| 5,532,462 | 7/1996 | Butwell et al. | 219/695 |
| 5,659,874 | 8/1997 | Rault et al. | 422/186 |
| 5,672,316 | 9/1997 | Knapp | 422/21 |

OTHER PUBLICATIONS

Kingston et al., Microwave Enegry For Acid Decomposition . . . American Chemical Society, pp. 2534–2541 (1986).
Kingston et al., Introduction to Microwave Sample Preparation, pp. 9–15 and pp. 93–154 (1988).
Margolis, The Hydrolysis of Proteins by Microwave Energy, Journal of Automatic Chemistry, pp. 93–95 (May.–Jun., 1991).
Mingos et al., Applications for Microwave Dielectric Heating Effects to Synthetic Problems in Chemistry, Chem. Soc. Rev., pp. 1–47 (1991).
Kingston et al., Comparison of Microwave versus Conventional Dissolution for Environmental Applications, Spectroscopy, pp. 20–27 (Nov./Dec. 1992).
Onuska et al., Extration of Pesticides form Sediments Using a Microwave Techinique, Chromatographic, vol. 36, pp. 191–194 (1993).

*Primary Examiner*—Daniel J. Jenkins
*Attorney, Agent, or Firm*—Arnold B. Silverman; Eckert Seamans Cherin & Mellott, LLC

[57] ABSTRACT

A method of microwave assisted chemical reaction includes providing a microwavable reaction vessel which contains at least one material in a sample. The sample is heated by microwave energy to elevate the temperature of the reagent and at least partially volatilize the sample to establish a gas phase within the vessel followed by positive cooling of the gas phase to reduce the temperature and responsively reduce the pressure of the gas phase without effecting substantial cooling of the liquid phase. The method may involve employing cooling exteriorly of and adjacent to the gas phase containing portion of the vessel or cooling by means of a coolant flowing within coils disposed in the interior of the vessel or both. The process is preferably a continuous process. The apparatus may be a vessel transparent to microwave energy for receiving the sample. The vessel has space overlying the liquid phase containing portion for a gas phase. Structures for cooling means for positively cooling the gas phase to reduce the pressure of the gas phase without effecting substantial cooling of the reagent are provided. These structures for cooling may be contained within the vessel, exteriorly of the vessel or modification of the vessel configuration to facilitate gas phase cooling or combinations thereof.

14 Claims, 3 Drawing Sheets

METHOD AND APPARATUS FOR MICROWAVE ASSISTED CHEMICAL REACTIONS

CROSS REFERENCE TO RELATED APPLICATIONS

This is a division of application Ser. No. 08/458,757 filed Jun. 2, 1995 pending which is a continuation-in-part of U.S. patent application Ser. No. 08/357,097, filed Dec. 15, 1994, entitled "Method and Apparatus for Microwave Assisted Chemical Reactions," now abandoned which is a continuation of U.S. patent application Ser. No. 08/127,263, filed Sep. 24, 1993, entitled "Method and Apparatus for Microwave Assisted Chemical Reactions" now abandoned.

BACKGROUND OF THE INVENTION

1. Field of the Invention

This invention relates to a method of microwave assisted chemical reactions, such as sample preparation, synthesis, derivatization or extraction which involves reduced pressure within the vessel and associated apparatus for accomplishing this objective.

2. Description of the Prior Art

The use of microwave energy in analytical chemistry to provide heat to assist chemical reactions has been known for approximately 15 years. See, generally, Mingos et al., Applications of Microwave Dielectric Heating Effects to Synthetic Problems in Chemistry, Chem. Soc. Rev. 1991, 20, pp. 1–47.

It has been known to employ such microwave heating in sample preparation. See, Kingston et al., Comparison of Microwave Versus Conventional Dissolution of Environmental Applications, Spectroscopy 7 (9) November/December 1992, pp. 20–27. One approach involves an open-vessel approach in which the result is achieved with the assist of microwave heating. An alternate approach is the so called "closed-vessel" microwave sample preparation.

It has been know to use microwave energy for various types of environmental processes. For example, microwave energy, such as that produced by a nominal or high intensity microwave oven, has been employed to extract pesticides from sediment samples. See, Onuska et al., Extraction of Pesticides from Sediments Using a Microwave Technique, Chromatographia, Vol. 36, pp. 191–194 (1993). Microwave heating has also been employed in effecting hydrolysis of proteins. See, Margolis et al., The Hydrolysis of Proteins by Microwave Energy, Journal of Automatic Chemistry, Vol. 13, No. 3, pp. 93–95 (May/June 1991).

It has also been known to employ microwave energy in a closed vessel digestion system wherein a closed Teflon PFA vessel has an organic sample, an inorganic sample or a combination subjected to acid decomposition under the influence of microwave energy. See, Kingston et al., Microwave Energy for Acid Decomposition at Elevated Temperatures and Pressures Using Biological and Botanical Samples, Anal. Chem., 58, pp. 2534–2541, (October, 1986).

In such closed vessel microwave sample preparation techniques, typically, one or more materials which will become the sample are mixed or dissolved in a suitable liquid reagent. The liquid reagent occupies a portion of the volume of the relatively small vessel and is subjected to chemical alteration under the influence of the microwave heating, thereby creating a gas phase in addition to the liquid phase within the vessel. The microwave heating results in increased temperatures and pressures within the vessel which can present a potential safety hazard through vessel failure. The increased temperature is required for advancement of the reaction rate, but the pressure is a property of the heat flow characteristics of the vessel and microwave interaction.

It has been known to control heat loss from the vessel by providing a jacket of thermal insulation around the vessel which also acts to strengthen the vessel. See, generally, Mingos et al., Applications of Microwave Dielectric Heating Effects to Synthetic Problems in Chemistry, Chem. Soc. Rev., 1991, 20, pp. 1–47 and Chapter 6, Introduction to Microwave Sample Preparation Theory and Practice by Kingston et al., American Chemical Society, 1988, pp. 93–154.

U.S. Pat. No. 5,215,715 discloses a method of digesting materials which are dispersed in an acid digesting medium, which dispersion is subjected to microwave heating in a first chamber and then both the gas and liquid phases of the dispersion are cooled in another chamber. There is no segregated cooling of the gas phase while heating the liquid phase. There is also no recognition of the pressure relationship between the gas phase and liquid phase during microwave radiation.

In prior art practices, pressure within the vessel has been permitted to form at whatever natural level occurred due to the specific reagents, temperature, reaction products, microwave interaction and heat flow of the vessel.

There remains, therefore, a very real and substantial need for a more efficient and safe means of microwave sample preparation in a closed vessel.

SUMMARY OF THE INVENTION

The present invention has solved the above-described problems by providing a method and apparatus wherein a microwavable reaction vessel is provided with a liquid reagent mixture and/or sample. For convenience of reference herein, both of these categories and any similar materials to be processed will be referred to as a "sample." The sample is heated so as to elevate the temperature thereof to establish at least partial volatization of the sample and thereby create a gas phase overlying the liquid reagent within the vessel. The gas phase is positively cooled to reduce the temperature in the gas phase and, responsive to said temperature reduction, reducing the pressure without effecting substantial cooling of the liquid reagent.

The cooling of the gas phase may be effected by providing channels for coolant flow exteriorly of the vessel or coolant flow within the vessel within coils or both. In this manner, the temperature and pressure of the gas phase are reduced in the preferred practice of the invention, while the coolant flowing in the cooling conduits, whether they are disposed interiorly or exteriorly of the vessel or both, does not directly cool the liquid reagent.

The apparatus for practicing the method preferably includes a vessel, such as a vessel or vessel liner made from a suitable polymer or fluoropolymer, such as polytetrafluoroethylene, TFM or perfluoroalkoxy, which is transparent to microwave energy and receives the liquid reagent mixture and/or sample. The vessel may also utilize an outer casing of a different material, such as polyetherimide, glass filled polyetherimide, and other suitable materials. The vessel has additional capacity for the gas phase. Cooling means provide for positive cooling of the gas phase to reduce the temperature and pressure of the gas phase. The cooling means has passageways for the flow of coolant. The passageways may be disposed exteriorly of the vessel and adjacent to the outer walls of the vessel with the passageways not being disposed adjacent to the sample or liquid reagent containing portion of the vessel. In another embodiment, the passageways are coils disposed within the gas phase portion of the vessel.

It is an object of the present invention to provide a method and apparatus for closed vessel microwave assisted chemical reactions which effectively reduces the pressure in the gas phase within the vessel.

It is another object of the invention to provide such a system wherein the pressure reduction in the gas phase is effected through positive cooling to reduce the temperature thereof.

It is another object of the present invention to provide such a system which may be employed in microwave digestion and reaction bombs.

It is a further object of the present invention to provide such a system which is employed in preparing chemical samples for later analysis.

It is a further object of the invention which permits microwave heating of the sample to elevate its temperature simultaneous with positive cooling of the gas phase.

It is yet another object of the invention to provide such a system which is adapted to accomplish sample preparation in a much more rapid manner than those previously known.

It is a further object of the present invention to provide such a system which will contribute to increased durability of the vessels.

These and other objects of the invention will be more fully understood from the following description of the invention on reference to the illustrations appended hereto.

DESCRIPTION OF THE PREFERRED EMBODIMENTS

Figure 1:
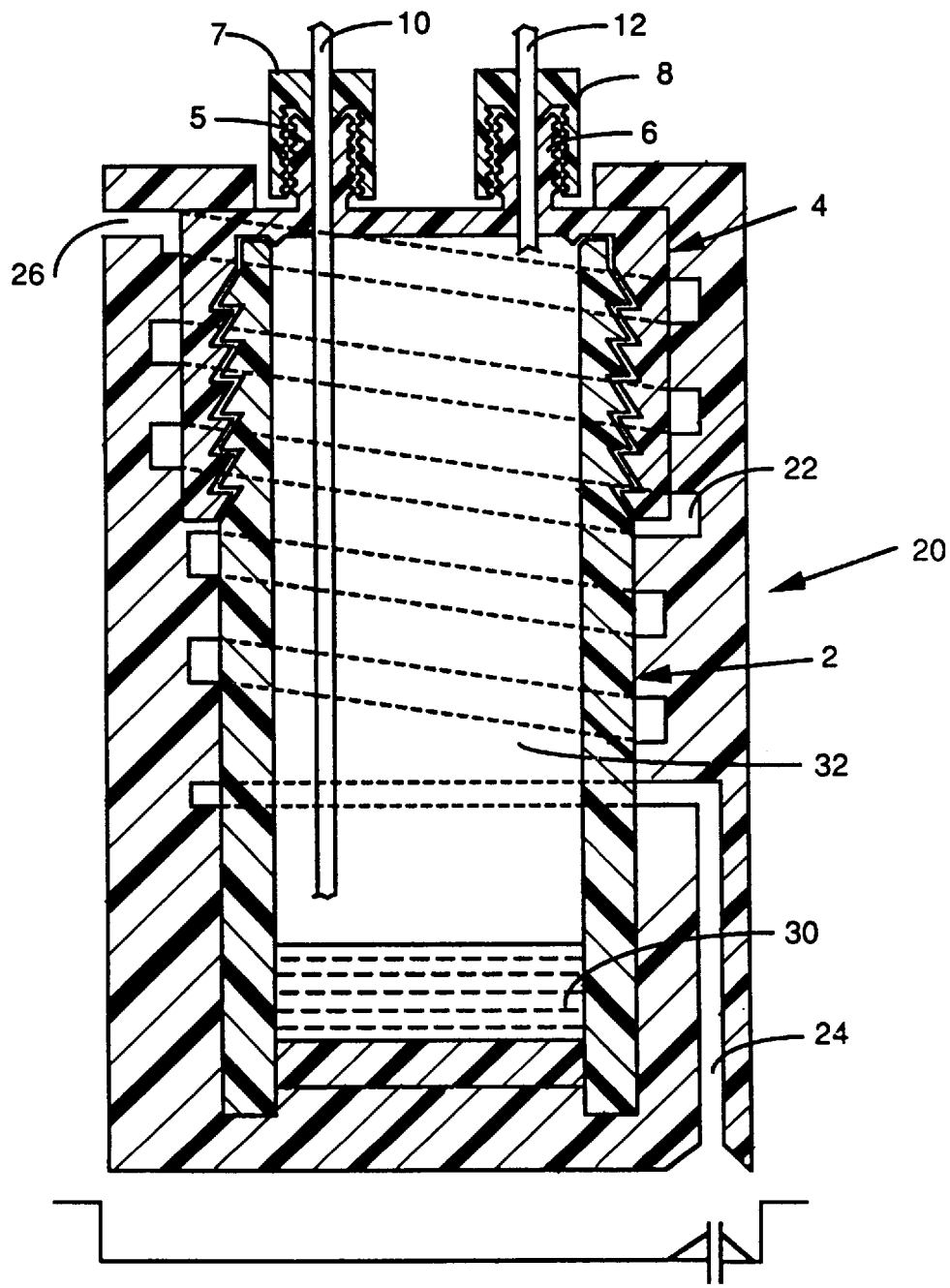
FIG. 1 is a schematic cross-sectional illustration of a form of vessel of the present invention having external cooling passageways.

Microwave vessels employed in chemical reactions, such as sample preparation, synthesis, derivatization and extraction generally are of relatively moderate size and may have an interior volume of about 1 mL to 500 mL and preferably in the range of about 1 mL to 125 mL. The vessels may have any desired configuration, but are frequently generally cylindrical in shape. They may be made of Teflon (tetrafluoroethylene, PFA or TFM or PTFE) or other fluorinated carbon plastics with a removable lid adapted to seal in place as by threaded or pressure fitted securement to maintain the desired amount of pressure, which for this type vessel, might be in the order of up to about 10 atmospheres. Another type of vessel would have a plastic casing for rigidity and pressure stability with a Teflon, plastic or quartz liner for chemical inertness and be adapted to withstand pressures of about 5 to 20 atmospheres. In this latter category, the vessel may be designed so as to withstand pressures of 40 to 100 atmospheres.

Closed vessel digestion will generally achieve higher temperatures because the boiling point of the reagent is raised by the pressure produced within the vessel. The higher temperature in the closed vessel will, however, greatly reduce the time required for reaction. The closed vessel also resists evaporation and there is, therefore, no need to add reagent to maintain the desired volume.

The vessels are effectively transparent to microwave energy so as to permit them to be introduced into a microwave oven and the reagents and samples contained in them to be heated to the desired temperature. As the liquid reagent containing one or more materials is heated, a gas phase is formed through the vaporization of the solvent and/or the chemical materials. The sample or samples will generally be mixed with a liquid reagent which may, for example, be nitric acid employed in microwave-heated digestions. In order to maintain pressure levels within the desired ranges of safety and contribute to durability of the vessels, as well as achieving the desired temperature which is most beneficial for the chemical reaction contemplated, the present invention provides positive cooling to the gas phase contained within the vessel while resisting effecting meaningful cooling of the liquid reagent.

For a given liquid reagent, the absorption of microwave energy can be calculated at a specific frequency employing Equation 1.

$$P\text{absorbed} = \frac{KC_p m \Delta T}{t} \quad (1)$$

wherein:

P= is the apparent power absorbed by the sample in watts (W), (W=joules/sec);

K= is the conversion factor for thermochemical calories/sec to W, which is 4.184;

$C_p$= is the heat capacity, thermal capacity, or specific heat (cal./g.$\Delta$C);

m= is the mass of the sample in grams (g);

$\Delta T$= is $T_f$, the final temperature minus $T_i$, the initial temperature ($\Delta$C); and t= is the time in seconds (s).

$$T_f = T_i + \frac{P\text{absorbed} \cdot t}{K \cdot C_p \cdot m} \quad (2)$$

$$T_f = T_i + \frac{P\text{absorbed} \cdot t}{K \cdot C_p \cdot m} - \text{HeatLoss} \quad (3)$$

In the event that no energy is permitted to escape from the vessel, the final temperature can be determined by equation 2.

As shown in Equation 3, a lower temperature is achieved if energy is permitted to escape. This escape can be primarily from the gas phase as it has the greatest area of cool vessel wall to contact.

In the present invention, active cooling of the gas phase serves to reduce the gas phase pressure. If desired, the microwave energy applied to the liquid phase sample may be increased to compensate for the thermal energy losses to the gas phase.

Referring now more specifically to FIG. 1 wherein there is shown a closed microwave reaction vessel which may be adapted for use with automation or a robot as distinguished from individual human handling, if desired. There is shown a vessel consisting of a liner 2 which may be composed of a suitable fluorinated carbon plastic, such as tetrafluoroethylene which is sold under the trade designation "Teflon" or other material having suitable strength, microwave transparency, and chemical inertness. The vessel liner 2 has a threaded closure 4 intimately secured in sealing relationship to the liner 2. The closure 4, in the form shown, has a pair of upwardly projecting, threadedly secured port defining members 5, 6 to which apertured closures 7, 8, respectively, are secured. While these port closures 7, 8 may be closed off if desired, in the illustrated embodiment temperature probes 10, 12, respectively, extend into the vessel 2 to different depths. These probes 10, 12 may be of any conventional type and are sealingly secured to the port closure 5, 7, 8.

Positioned in surrounding relationship with respect to liner 2 is an outer wall or casement 20 which is in intimate surface-to-surface contact with the exterior of the vessel 2 and closure 4. The casement 20 may be provided in multiple pieces (not shown) assembled around the vessel by any desired means known to those skilled in the art. The vessel 2, closure 4, and outer wall 20 are preferably of generally cylindrical configuration. The outer wall or casing 20 has an inwardly open continuous helical groove 22 which cooperates with exterior of the vessel liner 2 and closure 4 to create a continuous coolant flow passageway. The passageway is spaced (measured along the vessel longitudinal axis) from the sample liquid reagent received portion 30 of the vessel. A coolant entry channel 24 is defined within casement 20 and is in communication with passageway 22. Coolant is discharged through exit channel 26. The coolant will preferably be captured as it emerges from channel 26 and subjected to a heat exchanging temperature reduction after which it may be reintroduced into coolant entry channel for another cycle of operation. The coolant may be microwave non-absorbing, moderately absorbing, or strongly absorbing material that may be in a gas or a liquid phase.

If desired, the coolant passageways may be provided in other ways. For example, such as by a single ring, which is inwardly open to provide an annular passageway in cooperation with or adjacent to the exterior of the vessel. Also, an axially elongated single ring or a plurality of such rings either interconnected or individually supplied with coolant may be employed.

Figure 2:
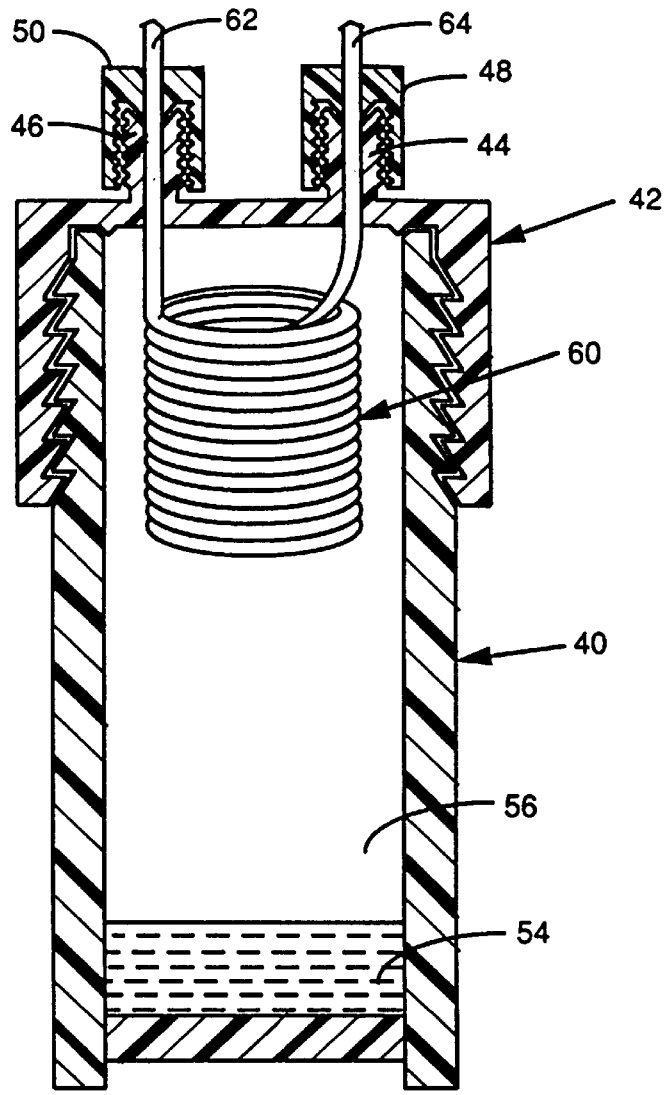
FIG. 2 is a schematic cross-sectional illustration of a form of vessel of the present invention having internal cooling passageways.

Referring now to FIG. 2 in greater detail there is shown a microwavable vessel 40 having threadedly and sealingly secured thereto a closure 42 which has a pair of externally threaded ports 44, 46 to which are secured threaded sealing closures 48, 50 respectively. The liquid reagent mixture or sample 54 is contained within the lower portion of the vessel interior and the gas phase 56 appears thereabove. A coolant coil 60 is received within the interior vessel 40 and has an entry end 62 and a discharge end 64. In effecting cooling of the gas phase 56 without effecting substantial cooling of the liquid reagent mixture 54, coolant is permitted to flow into entry 62, assume a heat exchanging interaction with the gas phase and then emerge at an elevated temperature at discharge end 64. The coolant coming out of end 64 is subsequently subjected to a heat exchanging process wherein the temperature of the coolant is reduced after which the coolant is reintroduced through entry 62. It will be appreciated that, in this manner, continuous cooling of the gas phase will be effected to thereby reduce the pressure within the gas phase 56. If desired, coils of additional length or multiple coils having separate entries may be employed. If desired, radiator structures may be employed in the vessel interior in lieu of the coil or coils.

It will be appreciated that the embodiment shown in FIGS. 1 and 2 are not mutually exclusive and that the coil or coils employed in connection with the embodiment of FIG. 2 may be employed in addition to the passageway containing outer wall 24 of FIG. 1 in order to achieve the desired degree of temperature reduction of the gas phase and corresponding reduction of pressure in the vessel interior.

The partial traditional equilibrium pressures and the partial pressures of the reagents and sample and reaction byproducts do not hold in this system as equilibrium of temperature between liquid and gas phases is never reached. Condensation of several components may occur reducing the partial pressure of one or more thus reducing the total pressure in the vessel. A dynamic nonequilibrium condition is established that is unique to microwave reagent closed vessel systems such as these and is a new relationship that is being employed to produce these new reaction conditions.

Figure 3:
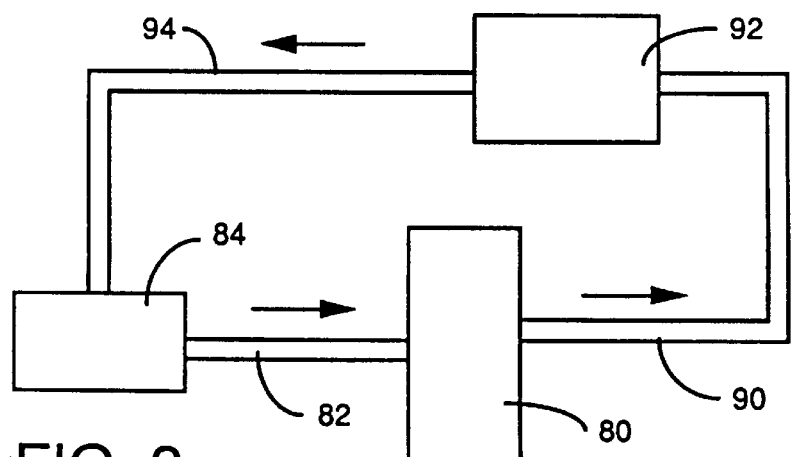
FIG. 3 is a schematic flow chart showing a continuous system of the present invention.

Referring now to FIG. 3, there is shown schematically a block diagram of a continuous or semi-continuous flow system of the present invention. The gas phase portion of vessel 80 receives coolant through pipe 82 by means of pump 84. After the coolant absorbs heat from the gas phase contained within vessel 80, the elevated temperature coolant emerges through pipe 90 and enters heat exchanger 92 wherein heat is withdrawn and the coolant is reduced to a temperature desired for introduction into the gas portion of vessel 80. The reduced temperature coolant emerges from the heat exchanger 92 and is carried by pipe 94 to pump 84 for reintroduction into vessel 80.

Figure 4:
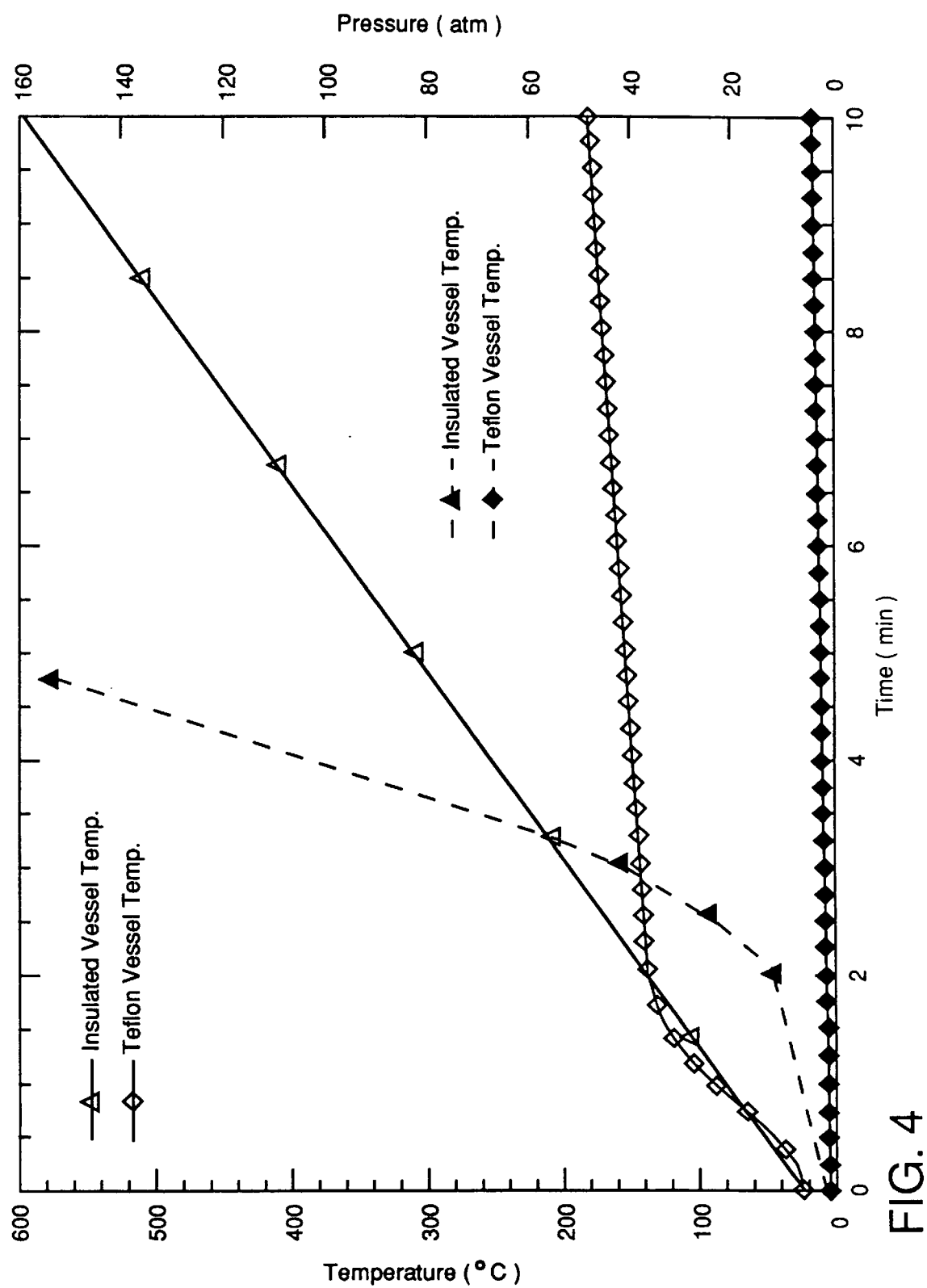
FIG. 4 is a comparison of reaction conditions in Teflon and insulated vessels.

Referring to FIG. 4, there is shown a plot of temperature in degrees centigrade and pressure in atmospheres as related to time. It compares a thermally insulated vessel with a thermally uninsulated vessel, i.e., a Teflon vessel. The difference in pressure inside the vessels is due to the loss of thermal energy in the gas phase. For example, the pressure of 6* 10 mL of concentrated nitric acid irradiated at 574 watts for 10 minutes at 180° C. is about 40 psi in the insulated vessel and is only about 8 psi in the uninsulated vessel. The absorption of microwave energy which can be calculated from equation 1 is the same for a given liquid.

EXAMPLE

In order to enhance the understanding of the invention, an example will be provided. A closed microwave vessel having an interior volume of 120 mL is provided with 20 mL of nitric acid mixed with a 0.5 gram liver tissue (material) in a closed vessel acid digestion process. The vessel was exposed to 500 watts of microwave energy for a period of 10 minutes to establish a liquid temperature of 190° C. and a liquid partial pressure inside the vessel of 620 psi without cooling. When a similar situation is constructed with cooling of the gas phase, there was established a pressure with the acid and digestion products of 120 psi inside the vessel. This demonstrates positive cooling by a method of the present invention employing a method of air coolant to produce after 10 minutes a gas phase temperature of 130° C. and a gas phase partial pressure of 120 psi without effecting a substantial reduction in the liquid phase temperature. A 650 watt power was applied in the second example to maintain the liquid temperature at 190° C. As a result, the acid digestion was effected while reducing the vessel pressure by 500 psi.

The coolant may be a gas or liquid with or without entrained solids, and is preferably transparent to microwave energy. Among the preferred coolant, materials are one or more materials selected from the group consisting of air, $CO_2$, freon, gaseous $N_2$ and liquid $N_2$.

The system of the present invention builds upon and enhances certain scientific principles as applied to solve a particular problem. The unique nature of microwave interaction and two distinct heat transfer mechanisms permits the cooling of the gas phase while continuing to heat the liquid phase. Heating a liquid in a microwave field is commonly referred to as dielectric loss. The two primary mechanisms are dipole rotation and ionic conduction. See, generally, Kingston, H. M. and Jassle, L. B., Eds., "Introduction to Microwave Sample Preparation: Theory and Practice," ACS Professional Reference Book, American Chemical Society, Washington, D.C., 1988, pp. 9–15. Ionic conduction is the conductive migration of dissolved ions in the applied electromagnetic field. Dipole rotation is the alignment, due to the electric field, of molecules that have permanent or induced dipole moments. When a molecule vaporizes and is converted to the gas phase, from the liquid phase, charged ions are left in the liquid phase, thereby eliminating this heating mechanism. In addition, rotation of the molecule in the gas phase does not efficiently transfer heat, as rotation without collision, does not add heat to the gas phase. Gas molecules frequently collide with the surfaces of the vessel. These surfaces are not heated by microwave energy and are actively cooled, thereby cooling the gas phase. The vessel is generally made of a material which is usually essentially microwave transparent. The gas phase is not efficiently heated by the microwave field even though the gas phase and liquid phase both exist in the same microwave field. These heating conditions are unique to the microwave environment. The present invention employs the ability to cool the gas phase while continuing to heat the liquid phase in this environment. The present invention involves intentionally cooling the gas phase while heating the liquid phase to effect the reduction of the internal vessel pressure while maintaining a relatively high liquid temperature in which various chemical reactions are conducted.

It will be appreciated, therefore, that the present invention provides a method and apparatus for pressure control and reduction in microwave-assisted chemical reaction systems. This is accomplished through positive cooling of the gas phase which is in contact with the liquid phase in the chemical reaction vessels without effecting significant reduction in temperature of the liquid phase. The positive cooling of the gas phase facilitates corresponding pressure control of the gas phase in order to achieve the desired chemical or physical parameters during and following the reaction period. The reactions in the liquid phase can, therefore, be carried out without undesired interference as a result of the positive cooling of the gas phase. The practice of the present invention will generally reduce the pressure in the gas phase about 50 to 95 percent and preferably about 60 to 90 percent. If desired, positive cooling action may be terminated or regulated when the desired gas phase pressure has been attained.

It will be appreciated that the present invention permits efficient thermally activated chemical reactions to occur at the desired temperature, while facilitating a reduction in pressure within the vessel at that temperature. This facilitates improved process efficiency, safety and durability. Improvement of the durability of the vessel is achieved through maintaining the integrity by resisting overheating of the casing in double walled vessels. Also, in the embodiment of FIG. 1, the coolant may serve to carry away sample or reaction products that might become trapped between the outer wall 20 and the vessel liner 2.

Also, if desired, the vessel might be formed with partially hollow outwardly projecting fins or ribs to facilitate radiation loss of heat from the gas phase. In the alternative, multi-walled vent openings may be provided in the outer wall to enhance cooling of the gas phase.

A plurality of circumferentially spaced, axially oriented ribs may be provided within the gas phase region of the vessel, but not in the liquid phase portion. such a construction will be deemed positive cooling within the context of the present invention.

In addition to the foregoing the turntable onto which the vessel is placed may be cooled. The hollow turntable top might have a recess which receives an upper portion of the vessel in intimate contact therewith. Coolant may be circulated within the hollow turntable top.

While not the preferred practice of the invention, if desired, gas may be withdrawn from the gas phase of the vessel, cooled and subsequently returned to the gas phase of the vessel.

The vessel may be a container that holds volumes from about 50 mL to 500 mL or may be an elongated tube which is closed to the atmosphere and in which the sample flows through the microwave field.

An elongated tube may have the sample and gas phase moving by the microwave source and cooling means so as to permit both heating of the sample and cooling of the gas phase which would be present in the sealed tube. As this embodiment would involve commingling of the liquid sample and gas phase, it is not the preferred embodiment.

It will be appreciated that the present invention may be employed advantageously with a wide variety of materials and end uses. The following examples will illustrate some advantageous uses. Among the specific end uses for which the sample preparation, method and apparatus of the present invention may be employed are microwave assisted decomposition, synthesis, derivatization and/or extraction or leaching. The invention may be employed to perform mineral acid decompositions while cooling the acid vapor to reduce the temperature and responsively the pressure of the decomposition system. Also, organic extraction with organic solvents may be performed while cooling the gas phase to reduce the pressure of the overall reaction.

The invention may be employed to perform organic or inorganic synthesis with solvents while cooling the gas phase to reduce the pressure during synthesis.

The invention may also be employed to perform hydrolysis on a protein with a solvent mixture including hydrochloric acid and cooling the gas phase to effect a reduction in pressure during hydrolysis. Another use is drying to condense components of the vapor phase.

In some instances, the gas phase may be cooled to resist temperature damage to the material out of which the inner liner or outer casings are made, such as polyetherimide, for example. The invention may also be employed with azeatropes, as well as aqueous materials.

Uses in environmental, biological, medical and industrial fields will be readily apparent to those skilled in the art.

The invention may be employed with all types of microwave systems including, for example, cavity-type microwave systems, focused microwave systems, flow and stop flow microwave systems, and antenna transmitted microwave cavities.

With respect to the liquid temperature, if desired one may operate at a higher liquid temperature with no increase in vessel internal pressure or at similar liquid temperatures with a decrease in pressure.

The invention further facilitates resisting undesired escape of the volatile elements, molecules, and compound losses when opening vessels to the atmosphere and condensing of these from the gas phase.

Whereas particular embodiments of the invention have been described herein for purpose of illustration, it will be evident to those skilled in the art that numerous variations of the details may be made without departing from the invention as defined in the appended claims.

I claim:

1. Apparatus for microwave assisted chemical reaction comprising, a vessel transparent to microwaves for receiving a sample containing at least one other material, said vessel having a space above the region wherein said sample will be present for receiving a gas phase, and cooling means for positively cooling said gas phase to reduce the temperature of said gas phase without effecting substantial cooling of said liquid phase.

2. The apparatus of claim 1 including said cooling means having at least one passageway through which coolant will flow to receive heat from said gas phase.

3. The apparatus for claim 2 including said passageways being disposed exteriorly of and adjacent to outer walls of said vessel, and said passageways not being disposed adjacent to the portion of said vessel in which said liquid sample will be received.

4. The apparatus for claim 2 including said passageways including coils disposed within the gas phase portion of said vessel interior.

5. The apparatus for claim 2 including means downstream of said passageways for removing heat from said coolant and returning said coolant to said passageways.

6. The apparatus for claim 1 including said vessel having an interior volume of about 1 mL to 500 mL.

7. The apparatus of claim 6 including said vessel or vessel liner being made of a fluoropolymer material.

8. The apparatus of claim 1 including an outer wall having an inwardly open groove which cooperates with the exterior of said vessel to define said passageway.

9. The apparatus of claim 8 including said passageway being axially spaced from the portion of the vessel in which said liquid sample will be received.

10. The apparatus of claim 2 including including said passageway being a continuous helix.

11. The apparatus of claim 1 including said cooling means including a plurality of hollow outwardly projecting ribs.

12. The apparatus of claim 11 including said ribs being generally axially oriented and being axially spaced from the section of said vessel containing said liquid sample.

13. The apparatus of claim 1 including said cooling means effecting reduction of the pressure of the gas phase responsive to said reduction in temperature.

14. The apparatus of claim 13 including said vessel being a closed vessel.

* * * * *